United States Patent
Van Rooijen et al.

[11] Patent Number: 5,968,790
[45] Date of Patent: Oct. 19, 1999

[54] INCREASED PRODUCTION OF CARBON DIOXIDE BY YEAST IN FLOUR-CONTAINING DOUGH

[75] Inventors: Rutger Jan Van Rooijen, Ede; Ronald Baankreis; Peter Johannes Schoppink, both of Amsterdam, all of Netherlands

[73] Assignee: Gist-brocades, N.V., Netherlands

[21] Appl. No.: 08/861,952

[22] Filed: May 22, 1997

Related U.S. Application Data

[63] Continuation of application No. 08/311,219, Sep. 23, 1994, abandoned.

[30] Foreign Application Priority Data

Sep. 24, 1993 [EP] European Pat. Off. .............. 93202753

[51] Int. Cl.$^6$ ................................. C12P 7/00; C12N 1/14
[52] U.S. Cl. ................... 435/132; 435/255.1; 435/172.3; 426/62
[58] Field of Search ................................ 435/132, 255.1, 435/172.3; 426/62

[56] References Cited

FOREIGN PATENT DOCUMENTS

WO 87/03006 of 1987 WIPO.

OTHER PUBLICATIONS

Navas, "Futile Cycles in Saccharomyces cerevisiae Strains Expressing the Gluconeogenic Enzymes During Growth on Glucose", Proc. Natl. Acad. Sci USA 90:1290–1294 (1993).
Rosenzweig, "Regulation of Fitness in Yeast Overexpressing Glycolytic Enzymes: Responses to Heat Shock and Nitrogen Starvation", Genet. Res. Camb. 59:166–177 (1992).

*Primary Examiner*—Irene Marx
*Attorney, Agent, or Firm*—Morrison & Foerster LLP

[57] ABSTRACT

Introduction of futile cycles in the glycolytic pathway of yeast strains enables enhanced gas production and ethanol production under stress conditions, e.g. in a sugar-rich dough having a sugar content of higher than 3% weight percentage based on flour, e.g. 20%, or at high ethanol concentration in an industrial ethanol production process.

2 Claims, 1 Drawing Sheet

INCREASED PRODUCTION OF CARBON DIOXIDE BY YEAST IN FLOUR-CONTAINING DOUGH

This application is a continuation of application Ser. No. 08/311,219 filed Sep. 23, 1994 now abandoned.

The present invention relates to improvement of gas and alcohol production by yeast.

Yeast strains, e.g. those belonging to the genus Saccharomyces, are used worldwide in the production of ethanol and leavening of bread. The yeast cell is equipped with a highly efficient machinery for the rapid fermentative conversion of fermentable sugars that are available in the dough, e.g. maltose, glucose and sucrose, into equimolecular amounts of $CO_2$ and ethanol. For many years, one of the major goals in yeast research has been the improvement of the $CO_2$ production rate of baker's yeast, which is commercially available as active dry 92–94%, instant dry 94–97%, compressed 26–33%, or cream yeast 15–21% dry matter. To this end, various classical hybridisation and molecular genetic approaches have been applied.

One such approach has been presented in published international application WO 87/03006. This application describes that the introduction into yeast cells of a process that reduces the cellular level of ATP stimulates glycolysis, presumably by stimulating those glycolytic steps in which ATP is generated. For this purpose, the fdp* gene was introduced into *Saccharomyces cerevisiae* and constitutively expressed. The mutant fdp* gene encodes a modified form of the gluconeogenic enzyme fructose-1,6-bisphosphatase (FBPase), in which Ala replaces Ser-12 thereby preventing allosteric negative control during growth on glucose. In addition, to prevent transcriptional repression during growth on glucose, the fdp* gene was placed under control of the constitutive gpdh promoter. In this way, a futile cycle was introduced in the glycolytic pathway of *Saccharomyces cerevisiae* at the level of the phosphofructokinase enzyme, resulting in the net hydrolysis of ATP. At the end of the anaerobic growth cycle, significantly higher $CO_2$ production (25% higher) was observed. However, no increase in $CO_2$ production was observed during the exponential growth phase of anaerobic growth. In lean dough (0–2% sugar), no or only a slight increase in $CO_2$ production rate was observed. Therefore, the use of the fdp* gene alone for the improvement of gas production in lean dough is of limited value since any improvement will likely be confined to the end of the fermentation.

Angeles Navas et al. (Angeles Navas, M., Cerdan, S., and Gancedo, J. M. (1993) Futile cycles in *Saccharomyces cerevisiae* strains expressing gluconeogenic enzymes during growth on glucoase, Proc. Natl, Acad. Sci. U.S.A. 90, 1290–1294) have studied the effect of the introduction of two different ATP-consuming reactions into *Saccharomyces cerevisiae* on $CO_2$ production rate. The fdp gene, the pck gene or both genes were introduced on multiple copy plasmids into *Saccharomyces cerevisiae* and the physiological effects were studied. The pck gene encodes the gluconeogenic enzyme phosoenolpyruvate carboxykinase (PEPcarboxykinase), which catalyses the formation of PEP from oxaloacetate at the expense of 1 ATP. Both genes were expressed constitutively under control of the adc promoter. Carbon dioxide and ethanal production were determined in resting cells containing no, one or both futile cycles. A significant increase in $CO_2$ and ethanol production rates were observed only with cells containing both futile cycles. However, during growth of the same yeast cells under non-stress conditions, we have found no or only very slight increase in $CO_2$ production rate compared with the parental strain.

Surprisingly, we have now found, however, that the gassing power of a yeast, especially baker's yeast, is strongly increased when at least one, preferably two, futile cycles are introduced into the yeast and the yeast is used for fermentation, e.g. in dough, under conditions that give rise to stress to the yeast. In addition, it has been surprisingly found that the presence of these futile cycles significantly improves the resistance of the yeast to drying.

By a futile cycle is meant the simultaneous occurrence of a catabolic and a corresponding anabolic biochemical reaction, in which ADP and ATP are generated, respectively, resulting in the net hydrolysis of ATP (see for example WO 87/03006). Examples of futile cycles useful in the present invention are constitutive fructose-1,6-bisphosphatase and PEP-carboxykinase activities.

By stress of a yeast is meant subjection of the yeast to conditions which have a negative effect on fermentative capacity, i.e. carbon dioxide and ethanol production rates. Stress factors for yeast include (i) high osmotic pressure due to a high sugar concentration and/or a high salt concentration (e.g. in a dough a sugar content of higher than 3%, e.g. about 20% or higher, and a salt content of about 1 to 4%, weight percentages based on flour), (ii) presence of a weak acid (e.g. in dough presence of calcium propionate e.g. at about 0.1% or higher, e.g. up to 0.6%, weight percentage based on flour, (iii) low pH (between 1 and 4), (iv) high ethanol concentration (above 5%) (v) nutrient starvation e.g. inorganic compounds such as nitrogen or phosphate (vi) high temperature and (vii) low water activity (between aw 0.62 and 0.90).

Thus, one aspect of the present invention is the use of a yeast which carries out at least one futile cycle, preferably two futile cycles, for fermentation under conditions such that the yeast is subjected to one or more stress factors for $CO_2$ and ethanol production.

The invention may find application not only with doughs, but also with other fermentation systems in which yeast stress factors may arise, e.g. in a fermentation system for industrial ethanol production from hydrolysed starch (see Example 5). Transformed yeast strains which may find use in accordance with the invention include not only transformed strains of Baker's yeast having a constitutively expressed FDPase gene and/or a constitutively expressed PEP carboxykinase gene, but also, for example, wine and whiskey yeast strains transformed to exhibit one or two futile cycles in the glycolytic pathway.

For the application for the invention to proving of doughs, Baker's yeast *Saccharoymces cerevisiae* having introduced both a constitutively expressed FDPase gene and a constitutively expressed PEP carboxykinase gene under the control of a constitutive strong promoter will most preferably be employed. The genes for the provision of the desired two futile cycles may be introduced into the yeast cells and stably maintained on multi-copy plasmids. Alternatively, the FDPase gene and PEPcarboxykinase gene may be integrated as a single copy or multi-copy gene into the host cell genome.

After introduction into Baker's yeast of genes encoding futile cycle enzymes as above, an increase in gas production can be observed in dough containing high sugar (higher than 3%, e.g. about 20% or higher, e.g. up to about 30%), high salt (about 2% or higher, e.g. about 2 to 4%), or calcium propionate (e.g. up to about 0.6%), whereas in their absence these stress conditions result in a significant decrease in gas production. The effects observed in sugar rich doughs containing propionate have been found to be synergistic, resulting in a significant increase in gas production compared to that of the parental strain.

The present inventors have thus established that futile cycles can be advantageously employed to increase the gas production of yeast cells in doughs under stress-inducing conditions such as high sugar and or salt concentration (osmotic stress), the presence of weak acid such as, for example, propionic acid, drying, low pH, high ethanol concentration. or nitrogen starvation. Such stress-conditions may occur in doughs for various known purposes and result in a decreased $CO_2$ production rate of yeast cells compared to the $CO_2$ production rate of non-stressed yeast cells in lean (e.g. 0% sugar) dough.

The examples below illustrate the invention with reference to baker's yeast containing two futile cycles. Use of such yeast to (i) improve industrial ethanol production and (ii) improve $CO_2$ production in doughs containing high sugar (20%), high salt (2%), calcium propionate (0.3%), pH 3.5, or combinations thereof.

*Saccharomyces cerevisiae* DS6623 (CJM-152) has been deposited under the terms of the Budapest Treaty on the International Recognition of the Deposit of Microorganisms for the Purposes of Patent Procedure at Centraalbureau voor Schimmelcultures under Accession number CBS 457.97. The Address is Oosterstraat 1, P.O. Box 273, 3740 AG BAARN, The Netherlands.

Furthermore, an example is given which illustrates that the positive effect on the fermentative activity of a baker's yeast containing two futile cycles increases with increasing stress conditions.

Determination of carbon dioxide production a. In synthetic dough medium or buffer Cells of the yeast *Saccharomyces cerevisiae* were grown in filter sterilized (0.22 μm) Yeast Nitrogen Base (w/o amino acids, concentration according to DIFCO manufacturer) with 2% glucose, 0.1 mg/ml uracil (for strain CJM-152), 0.4 mg/ml leucin (for strain CJM-152), and 50 mM potassium phosphate pH 5.5. Late exponentially grown yeast cells (50 ml) were harvested, washed twice with water, and resuspended in water to a concentration of 5.4 mg dry weight/ml. Subsequently, 2.5 ml of the yeast suspension was added to 2.0 ml of synthetic dough medium (composition per liter: 110 g glucose, 3 g $(NH_4)_2SO_4$, 4 g $MgSO_4.7H_2O$, 4 g $KH_2PO_4$, 4 g casaminoacids, 4 g citric acid.laq, 45 g tri-sodiumcitrate.2aq, 10 mg vitamin B1 and B6, 40 mg nicotinic acid, 20 mg calcium pantothenate, and 0.02 mg biotin: pH 5.6) or MES buffer (200 mM, pH 5.6, 10% glucose) and incubated at 28° C. for 165 min. The $CO_2$ produced during the incubation was flushed from the solution by the carrier gas ($N_2$) and measured for 165 min using an infrared detector (Leybold-Heraeus). Total $CO_2$ produced and specific $CO_2$ production rates were calculated on-line.

b. In dough

The $CO_2$ production rates of *Saccharomyces cerevisiae* strains CJM-152 and CJM-186 were determined in 3% and 20% sugar doughs without any additives, or containing 2% sodium chloride or 0.3% calcium propionate. The doughs were prepared as follows:

3% sugar dough 2 g of compressed yeast (28.5% dry matter) or 600 mg of dried yeast, 62.5 g flour, 1.87 g sucrose (3% sugar relative to the flour) and 35 ml of distilled water (additive A), 1.25 g sodium chloride (additive B, 2% NaCl relative to the flour), or 0.19 g calcium propionate (additive C, 0.3% CaP relative to the flour), were mixed in a Hobart apparatus.

20% sugar dough 2 g of compressed yeast (28.5% dry matter) or 600 mg of dried yeast, 62.5 g flour, 12.5 g sucrose (20% sugar relative to the flour) and 35 ml of additive A, B or C, were mixed as described for the 3% sugar dough.

For the determination of the gas production at pH 3.5, 35 ml of a 1.38% lactate solution is added to the dough instead of 35 ml distilled water.

After preparation, the doughs were transferred to steel barrels that were equilibrated at 28° C. The barrels were closed, and after equilibration for 7 minutes, the $CO_2$ production was measured for 165 minutes using a $CO_2$ sensor.

Manufacture of compressed yeast and dried yeast

Cultures of yeast strains CJM-152, CJM-186 and CJM-189 (described in Angeles Navas, M., Cerdan, S., and Gancedo, J. M. (1993) Futile cycles in *Saccharomyces cerevisiae* strains expressing gluconeogenic enzymes during growth on glucose, Proc. Natl, Acad. Sci. U.S.A. 90, 1290–1294) were grown on mineral medium in a series of fermentors. Cells were cultivated in 10 l laboratory fermentors with a net volume of 6 l. During the fermentation, pH and temperature were maintained at desired values by automatic control. The cultivation conditions of the final fermentation were as follows: nitrogen was supplied to the fermentation as a 10% solution of $NH_3$ in water, the total amount of nitrogen kept at 10% of the carbon source supplied. The pH was maintained at 5.6 during the fermentation. In the case of CJM-152, leucine and uracil were supplied to the culture to facilitate growth. The yeast obtained by this fermentation was concentrated and washed with tap water in a laboratory nozzle centrifuge. Yeast creams were compressed to a dry matter content varying between 26 and 32%. The measured protein content (%N*6.25) varied between 45 and 55% as a consequence of different yields on the carbon source for equal amounts of ammonia supplied.

Drying of the compressed yeast was performed on a laboratory scale fluidbed dryer, consisting of a conical glass tube built on an air supply system. Details of the procedure can be found for instance in U.S. Pat. No. 3,843,800. The dry matter content of the dried yeast was 96.5%.

Brief Description of the Drawing

The futile cycle stimulation factor (FCSF) as a function of the residual gas production (%) is shown.

EXAMPLE 1

Figure 1:
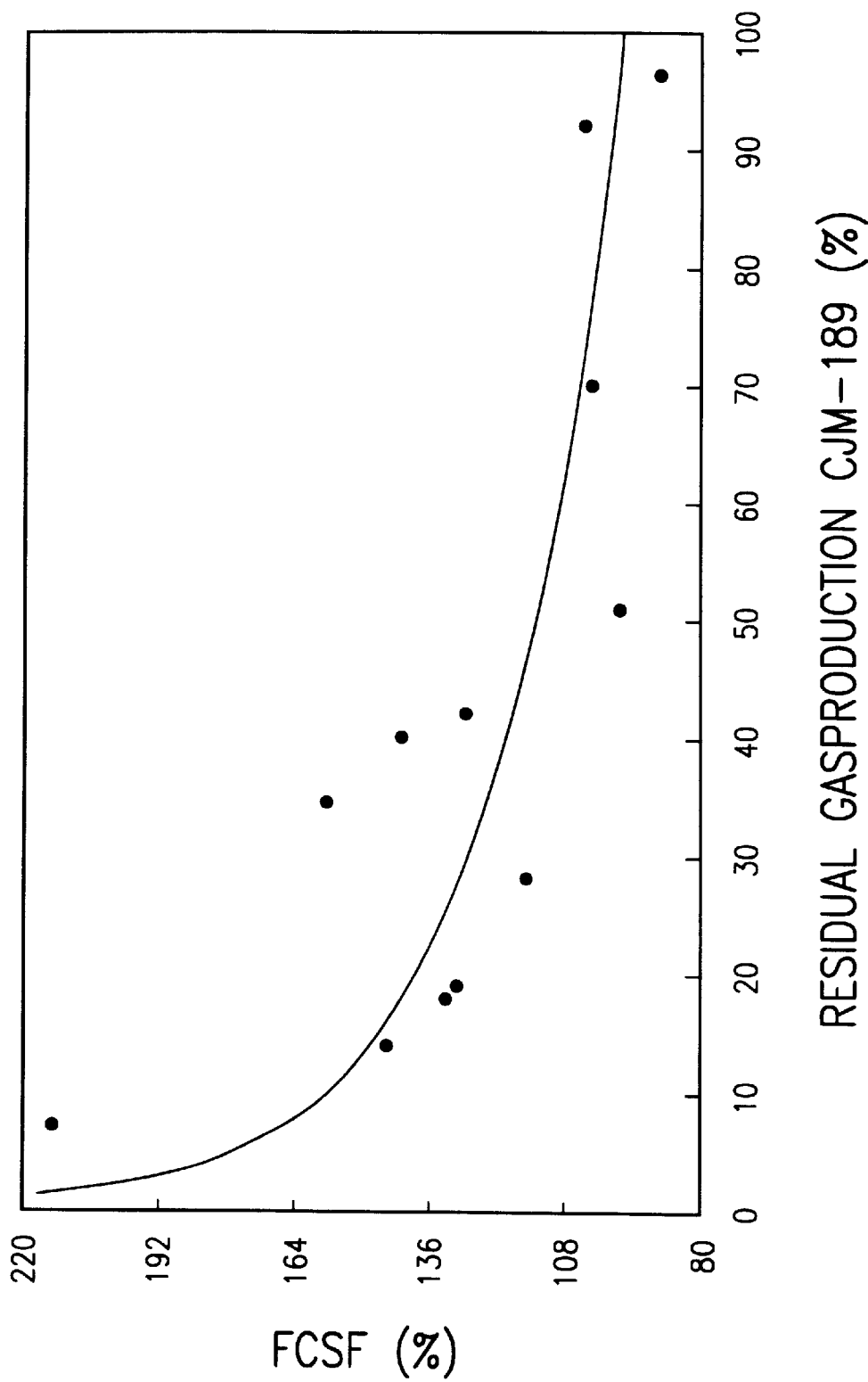

Improvement of gas production of stressed cells in synthetic dough medium after the introduction of two futile cycles In order to determine the increase of the $CO_2$ production rate in a synthetic dough medium after the introduction of two futile cycles in *Saccharomyces cerevisiae,* strains CJM-152 and CJM-186 were grown overnight at 28° C. in YNB medium as described above. pH values in the cultures were allowed to drop to pH 3.9 (from 5.6) or kept at pH 6.3 (from 6.6 by the addition of 100 mM potassium phosphate. $CO_2$ production rates were measured (Table 1) in complete medium with glucose as a carbon source and in MES buffer (pH 5.6) with glucose as described. The $CO_2$ production on complete medium (excluding growth) was significantly higher than that in buffer. Under these relatively optimal conditions no differences in gas production rates were observed between CJM-152 and CJM-186 pregrown at pH 4.5. Surprisingly, cells of CJM-186 that were pregrown under stress-conditions at pH 2.6 and tested on complete medium showed significantly higher $CO_2$ production than those of the parental strain CJM-152 grown under similar conditions. In addition, when the cells were tested for $CO_2$ production in buffer containing glucose, CJM-186 consistently outperformed the parental strain CJM-152. These experiments show that the transformed strain CJM-186, containing two futile cycles, displays significant advantages with respect to gas production under conditions of cellular stress. This shows that futile cycles might be especially useful for the improvement of gas production of cells used under stress conditions. In the experiments described here these stress conditions might be caused or augmented by the absence of medium components in buffer and/or the history of the cells (pH) before the application phase ($CO_2$ measurements).

TABLE 1

$CO_2$ production (ml in 165 min) of cells grown in complete medium and buffer at pH 2.6 and 4.5

|  | CJM-152 | CJM-186 |
|---|---|---|
| Complete medium (pH 3.9) | 287 | 401 |
| Complete medium (pH 6.3) | 431 | 405 |
| Buffer (pH 3.9) | 144 | 307 |
| Buffer (pH 6.3) | 216 | 307 |

EXAMPLE 2
Improvement of sugar resistance of baker's yeast after the introduction of two futile cycles The effects on the sugar resistance of baker's yeast were determined after the introduction of the two futile cycles (Table 2). For this purpose, the parental strain CJM-152 and the transformed strain CJM-186 were grown in a fed-batch culture on synthetic medium. Subsequently, the cells were harvested and the $CO_2$ production in low (3%) and high (20%) sugar doughs was determined in a standard dough test (Table 2). Comparison of strains CJM-152 (-CaP) and CJM-186 (-CaP) showed a significant improvement of the relative $CO_2$ production level of strain CJM-186 in the high sugar dough (Futile Cycle Stimulation Factor equals 116%). Also in the presence of 0.3% calcium propionate a significant increase of sugar resistance was observed in strain CJM-186 (FCSF equals 206%). Futhermore, in strain CJM-186 a stimulation of $CO_2$ production in the 20% sugar dough was observed in the presence of 0.3% CaP (Table 2; 165', 99% vs 106%), whereas the parental strain exhibited a decreased $CO_2$ production (Table 2; 165', 84% vs 50%).

The experiments presented here indicate that in dough the presence of futile cycles in a yeast strain improves the resistance to high sugar concentrations both in the presence and absence of calcium propionate. This results in increased $CO_2$ production rates in high sugar doughs in comparison with those strains lacking these futile cycles.

EXAMPLE 3
Improvement of resistance to calcium propionate after the introduction of two futile cycles The effects of introduction into baker's yeast of two futile cycles with respect to $CO_2$ production in the presence of calcium propionate was studied. For this purpose, the $CO_2$ production rates of compressed cells of strains CJM-152 and CJM-186 were determined in 3% and 20% sugar doughs in the presence or absence of 0.3% calcium propionate. In Table 2 it is clearly shown that the transformed strain CJM-186 is superior with respect to propionate resistance compared to the parental strain CJM-152 both in the low (3%) and high (20%) sugar doughs. In the 3% sugar dough, the $CO_2$ production of the parental strain CJM-152 decreases considerably in the presence of CaP (84%, 165'), whereas the $CO_2$ production of strain CJM-186 is not affected (99%, 165'). In the 20% sugar dough, the $CO_2$ production of the parental strain CJM-152 was stimulated 1.4-fold (50:36; 165') by the addition of CaP, whereas a 2.5-fold (106:43; 165') stimulation was observed in the transformed strain CJM-186.

These experiments clearly show that in dough the resistance of a yeast strain against calcium propionate is positively affected by the presence of two futile cycles.

EXAMPLE 4
Improvement of resistance to sodium chloride after the introduction of two futile cycles In order to test the effects of two futile cycles on the salt resistance, the $CO_2$ production was determined of CJM-186 and the parental strain CJM-152 in 3 and 20% sucrose both in the presence and absence of 2% sodium chloride (Table 2). The addition of NaCl in dough with the parental strain CJM-152 resulted in a significant decrease of gas production both in the 3% and 20% sugar doughs, 20 and 4% of control value, respectively. In the case gene transformed strain CJM-186, a partial recovery of gas production was observed (FCSF 320%; Table 2).

The experiments presented here show that the introduction of two futile cycles into a yeast strain significantly improves the resistance to salt stress, yielding a higher $CO_2$ production rate compared to that or the parental strain lacking these futile cycles.

TABLE 2

Relative $CO_2$ production (%) after 100 and 165 minutes by strains CJM-152 and CJM-186 in 3% and 20% sugar doughs containing no (−CaP), 0.3% calcium propionate (+CaP), or 2% sodium chloride.

| Strain | CJM-152 | | CJM-186 | | |
|---|---|---|---|---|---|
| Conditions | 100 min | 165 min | 100 min | 165 min | FCSF |
| 3%, −CaP | 100 | 100 | 100 | 100 | |
| 3%, +CaP | 86 | 84 | 108 | 99 | 119 |
| 3%, +NaCl | 21 | 20 | 77 | 73 | 366 |
| 20%, −CaP | 41 | 36 | 46 | 43 | 116 |
| 20%, +CaP | 61 | 50 | 122 | 106 | 206 |
| 20%, +NaCl | 6 | 4 | 17 | 15 | 320 |

The futile cycle stimulation factor (FCSF) values were calculated by dividing the CJM-186 relative gas production values by those of CJM-152. The given FCSF is the mean value of those calculated for 100 and 165 minutes. The absolute $CO_2$ production rates of CJM-152 and CJM-186 after 165 minutes were 165 and 333 ml, respectively. Data are average values of four independent experiments.

EXAMPLE 5
The positive effect on the carbondioxide production of baker's yeast after te introduction of two futile cycles increases with increasing stress conditions This example supports the finding that the positive effect of the presence of two futile cycles (i.e. constitutive FBPase and PEPCK enzyme activities) on the gas production of baker's yeast increases when the stress conditions, that the yeast may face during the various applications in dough, increase.

Furthermore, in order to exclude the possibility that the positive effects described in the previous examples are a result of the presence of the plasmids as such, instead of the futile cycles genes, experiments were carried out with the isogenic parent strain CJM-189. In contrast to strain CJM-152 that is an isogenic parent without plasmids, strain CJM-189 contains the same plasmids as CJM-186, except for the coding regions of the FBPase and PEPCK genes. This strain including the plasmids are described in Angeles Navas et al. (1993, PNAS 90, 1290–1294).

The carbondioxide production rates in doughs during various stress conditions were determined of compressed cells of fed-batch grown strains CJM-186 and CJM-189.

Thirteen stress-conditions were tested:
0.3% CP#
20% sucrose
pH 3.5
0.3% CP, 2% NaCL
0.3% CP, pH 3.5
2% NaCl, pH 3.5
20% sucrose, 0.3% CP
20% sucrose, 2% NaCl
20% sucrose, pH 3.5
2% NaCl, 0.3% CP, pH 3,5
20% sucrose, 0.3% CP, 2% NaCl
20% sucrose, 0.3% CP, pH 3.5
20% sucrose, 2% NaCl, pH 3.5 # Calciumpropionate In lean dough (3% sucrose) without any additions the yeast showed the highest gas production rate. Therefore, these dough conditions were considered as the non-stress conditions.

The Figure clearly shows that the futile cycle stimulation factor (FCSF) increases as the residual gas production (as a cause of the applied stress) decreases.

The residual gas activity is the gas production of the isogenic control strain CJM-189 during the stress conditions tested, given as a percentage of the (identical) gas productions of strains CJM-186 and CJM-189 in lean dough (310 ml $CO_2$, 165 $min^{-1}$, 600 mg dry $matter^{-1}$; standard deviation: 4%), i.e. during non-stress conditions. The residual gas activity is correlated to the loss of fermentative activity due to the applied stress conditions, and is therefore correlated to the magnitude of the stress. For example, a residual gas production of 10% indicates that as a consequence of the applied stress condition 90% of the potential gas production is lost as a cause of this stress condition. The FCSF was calculated by dividing the residual gas activity of CJM-186 by that of the isogenic control strain CJM-189 and multiplication by 100 in order to obtain percentages. Therefore, a FCSF of 100 means that the presence of two futile cycles has no (positive or negative) effect on the gas production. A FCSF exceeding 100 indicates that the presence of two futile cycles stimulates the gas production by the percentage that is given. Datapoints were fitted using the SliteWrite 4.0 program. The stress conditions tested are indicated in the text.

The experiments described here clearly show that in dough the resistance of baker's yeast strains against the indicated stresses is positively affected by the presence of two futile cycles.

Furthermore, these experiments show that this positive effect increases as the magnitude of the stress increases.

EXAMPLE 6

After drying the positive effects of the presence of two futile cycles in baker's yeast are retained. Improvement of resistance to drying after the introduction of two futile cycles.

Since baker's yeast is also merchandised as active dry (ADY) or instant dry (IDY) yeast one of the prerequisites for the application of the 'futile cycle' technology is that the positive effects described above for compressed yeast are retained after drying.

Therefore, part of the compressed material of strains CJM-186 and CJM-189 (used for the experiments described above) was dried and tile gas production was determined under various stress conditions. Table 3 shows the results of these experiments.

TABLE 3

Gas productions in various doughs of yeast strains CJM-186 and CJM-189 after drying. The gas productions are given as percentages from the gas production of compressed yeast of the control strain CJM-189 in dough containing 20% sucrose without any other additions (207 ml $CO_2$, 165 $min^{-1}$, 600 mg dry $matter^{-1}$). Dryability was calculated by dividing the gas production of the dried yeast by that of the equal amount of dry matter in compressed yeast.

| Conditions | CJM-189 | CJM-186 | FCSF |
|---|---|---|---|
| Compressed, 20% sucrose | 100 | 121 | 121 |
| Dried, 20% sucrose | 37 | 58 | 157 |
| Dried, 20% sucrose, 2% NaCl | 24 | 49 | 204 |
| Dried, 20% sucrose, pH 3.5, 0.3% CP | 19 | 44 | 231 |
| Dryability | 37 | 48 | 130 |

From Table 3 it can be clearly extracted that after drying the positive effects of the presence of two futile cycles are retained. In addition, as in the compressed yeast, the impact of the futile cycles on the improvement of the gas production of dried yeast increases with increasing stress conditions. A FCSF of 157% in the 20% sucrose dough, that in this experiment is the 'least' stress condition, was found. The FCSF's are considerably higher after the additions of either 2% NaCl (FCSF 204%) or pH 3.5, 0.3% CP (FCSF of 231%), that are increased stress conditions as is evident from the lower gas productions.

Surprisingly, we have found that the dryability of the futile cycles containing strain CJM-186 also increased. The FCSF in this case was 130%.

The experiment presented here indicate that the positive effects of the two futile cycles on the gas production of compressed yeast that were described above also holds for dried yeast. In addition, the presence of two futile cycles also resulted in a significantly higher resistance of the yeast against drying.

EXAMPLE 7

Improvement of ethanol production from glucoamylase/amylase-treated starch in yeast by the introduction of two futile cycles For generation of fuel alcohol, glucose is used as a carbon/energy source and converted into ethanol. The glucose used can be generated by hydrolysis of starch by, for example, glucoamylase/amylase treatment. The starch used can be present, for example, in corn, molasses or maize.

Efficiency problems of this type of process are the relatively slow ethanol production rate resulting in a long fermentation time, and the low overall yield (i.e. the amount of ethanol formed from glucose).

These drawbacks can be explained in part by the relatively weak tolerance of conventionally employed yeast strains to ethanol stress, resulting in a decreasing ethanol production as a function of the increasing ethanol concentration. In addition, in the waste stream only limited nitrogen compounds are available that can be used as a nitrogen source. Therefore, stress as a consequence of nitrogen starvation at a certain stage in the alcohol fermentation probably also attributes to the relatively weak performance of yeast strains conventionally used in this process.

Surprisingly, we have found that the presence of two futile cycles in yeast strain CJM-186 significantly improves the ethanol production rate and yield, compared to that of the wild-type strain CJM-152. Table 4 shows the results of an experiment in which the ethanol production rate and total ethanol production of both the wild-type strain CJM-152 and the transformed strain CJM-186 were determined. Glucoamylase/amylase-treated waste stream containing starch was used as the energy/carbon source. Ethanol production rate and total ethanol production are given as percentages, with the results for wild-type strain CJM-152 normalised at 100%.

TABLE 4

The effect of two futile cycles on ethanol production rate and overall ethanol production by yeast grown on a glucoamylase-treated waste stream of a starch modification process.

|  | EtOH production rate | Total EtOH production |
|---|---|---|
| CJM-152 | 100 | 100 |
| CJM-186 | 119 | 122 |

We claim:

1. A method to increase the production of carbon dioxide by *Saccharomyces cerevisiae* in a flour-containing dough that causes stress on said *Saccharomyces cerevisiae* which method comprises inoculating said dough with a strain of *Saccharomyces cerevisiae* genetically modified so as to conduct at least two futile cycles in the anaerobic glycolytic pathway which results in increased $CO_2$ production under stress compared to the $CO_2$ production of its unmodified isogeneic parent *Saccharomyces cerevisiae* strain;

wherein the dough that causes stress on said *Saccharomyces cerevisiae* is selected from the group consisting of:

dough having a sugar content of about 3% or more by weight relative to weight of flour in said dough;

dough having a salt content of 1% or more by weight relative to weight of flour in said dough; and dough having a calcium propionate content of 0.1% or more by weight relative to weight of flour in said dough;

wherein said genetic modification causes the *Saccharomyces cerevisiae* strain, under stress, to constitutively express genes which increase amounts of carbon dioxide produced as compared to its isogenic *Saccharomyces cerevisiae* parent strain which has not been modified to conduct at least two futile cycles in the anaerobic glycolytic pathway, and subjecting the inoculated dough to conditions suitable for *Saccharomyces cerevisiae* growth.

2. The method of claim 1 wherein said two futile cycles are effected by modifying said *Saccharomyces cerevisiae* to constitutively express the gene for fructose-1,6-biphosphatase and the gene for phosphoenolpyruvate carboxykinase.

* * * * *